US012781188B2

(12) United States Patent
Shin

(10) Patent No.: US 12,781,188 B2
(45) Date of Patent: Nov. 3, 2026

(54) METHOD FOR ALIGNING AND CULTURING CELLS IN THREE DIMENSIONS

(71) Applicant: Pensees Inc., Seoul (KR)

(72) Inventor: Jaeha Shin, Seoul (KR)

(73) Assignee: Pensees Inc., Seoul (KR)

( * ) Notice: Subject to any disclaimer, the term of this patent is extended or adjusted under 35 U.S.C. 154(b) by 1007 days.

(21) Appl. No.: 17/596,961

(22) PCT Filed: Dec. 3, 2021

(86) PCT No.: PCT/KR2021/018256
§ 371 (c)(1),
(2) Date: Dec. 22, 2021

(87) PCT Pub. No.: WO2023/101071
PCT Pub. Date: Jun. 8, 2023

(65) Prior Publication Data

US 2024/0026298 A1 Jan. 25, 2024

(51) Int. Cl.

| | |
|---|---|
| ***B33Y 10/00*** | (2015.01) |
| ***B33Y 40/20*** | (2020.01) |
| ***B33Y 70/00*** | (2020.01) |
| ***C12N 5/077*** | (2010.01) |

(52) U.S. Cl.
CPC ............ *C12N 5/0658* (2013.01); *B33Y 10/00* (2014.12); *B33Y 40/20* (2020.01); *B33Y 70/00* (2014.12); *C12N 2513/00* (2013.01); *C12N 2533/70* (2013.01)

(58) Field of Classification Search
None
See application file for complete search history.

(56) References Cited

U.S. PATENT DOCUMENTS

| | | | | |
|---|---|---|---|---|
| 10,760,056 | B2 | 9/2020 | Kim et al. | |
| 2018/0208898 | A1 | 7/2018 | Kim et al. | |
| 2018/0280578 | A1 | 10/2018 | Hwang | |
| 2019/0142995 | A1* | 5/2019 | Ahn | A61L 27/38 264/129 |
| 2020/0108172 | A1* | 4/2020 | Skardal | A61L 27/48 |
| 2020/0189182 | A1* | 6/2020 | Compaan | B33Y 70/10 |

FOREIGN PATENT DOCUMENTS

| | | | |
|---|---|---|---|
| KR | 1020170011522 | A | 2/2017 |
| KR | 1020170012099 | A | 2/2017 |
| KR | 1020180027001 | A | 3/2018 |
| KR | 20180125776 | A * | 11/2018 |
| KR | 1020180125776 | A | 11/2018 |

OTHER PUBLICATIONS

Zhou et al (International Journal of Bioprinting, vol. 3(2): 130-137. Doi: 10.18063/IJB.2017.02.003, Jul. 11, 2017) (Year: 2017).*
Mccormack et al (Trends in Biotechnology, Jun. 2020, vol. 38, No. 6; Doi: 10.1016/j.tibtech.2019.12.020). (Year: 2020).*
Zhuang et al (PLoS One 14(6): e0216776. Doi: 10.1371/journal.pone.0216776, Jun. 12, 2019). (Year: 2019).*
Irvine et al (Biomed Microdevices (2015) 17: 16, DOI 10.1007/s10544-014-9915-8) (Year: 2015).*
The International Search Report and Written Opinion for PCT/KR2021/018256, 8 pages, mailed Aug. 29, 2022.
Fan et al., "Controllable assembly of skeletal muscle-like bundles through 3D bioprinting", Biofabrication, 2022, vol. 14, No. 1, p. 015009 (13 pages).
Office Action from corresponding Korean Patent Application No. KR 10-2021-0171885 A, mailed Jun. 19, 2024, with English translation attached.
Ghavaminejad et al., "Crosslinking Strategies for Three-Dimensional Bioprinting of Polymeric Hydrogels", Small. 2020; 16(35): e2002931, 62 pages.

* cited by examiner

*Primary Examiner* — Peter Paras, Jr.
*Assistant Examiner* — Khoa Nhat Tran
(74) *Attorney, Agent, or Firm* — Vorys, Sater, Seymour and Pease LLP; Mih Suhn Koh

(57) ABSTRACT

A method for aligning and culturing cells in three dimensions includes mixing cells with a hydrogel to prepare a bio-ink, outputting the bio-ink while moving a nozzle of a discharge device to form an output product having a pattern having at least parallel portions, curing the output product, and culturing the cured product. According to the present invention, cells may be cultured to a high density in a three-dimensionally aligned state along a parallel pattern, so that there is an advantage in that the texture of a tissue formed by the cells, for example, a unique texture of a muscle tissue, may be simulated or reproduced.

9 Claims, 4 Drawing Sheets

METHOD FOR ALIGNING AND CULTURING CELLS IN THREE DIMENSIONS

TECHNICAL FIELD

The present invention relates to a method for aligning and culturing cells in three dimensions.

BACKGROUND ART

The alignment of cells means that cells are stretched above a predetermined level and have directionality. In vivo, cells are naturally aligned not only by microscopic factors such as the surface structure of an extracellular matrix, but also by macroscopic factors such as the curvature or shape of a tissue, but it is not easy to reproduce such a phenomenon in an in vitro culture process.

Typically, for the aligned culture of cells as described above, a cell culture vessel is improved, and particularly, the culture vessel is designed to have a number of grooves or protrusions reflecting the surface structure of an extracellular matrix which are artificially formed on a culture surface of the culture vessel such that cells are cultured in an aligned state. However, since the culture surface is produced using photolithography, E-beam lithography, etc., there have been limitations in that the production cost is high and mass production is difficult, as well as in that it is not easy to form a culture surface capable of simulating a three-dimensional complex bio-environment with high precision.

Accordingly, there is a need for research and development of a technique capable of aligning and culturing cells using a typical culture vessel through improvement in methodological aspects, not through improvement of a culture vessel.

DISCLOSURE

Technical Problem

An aspect of the present invention provides a method for aligning and culturing cells in three dimensions.

Technical Solution

According to another aspect of the present invention, there is provided a method for aligning and culturing cells in three dimensions, the method including mixing cells with a hydrogel to prepare a bio-ink, outputting the bio-ink while moving a nozzle of a discharge device to form an output product having a pattern having at least parallel portions, curing the output product, and culturing the cured product.

Advantageous Effects

According to the present invention, cells may be cultured to a high density in an aligned state along a parallel pattern, so that there is an advantage in that the texture of a tissue formed by the cells, for example, a unique texture of a muscle tissue, may be simulated or reproduced.

However, effects to be obtained by the present invention are not limited to the effects mentioned above, and other effects not mentioned will be clearly understood by those skilled in the art from the following description.

DETAILED DESCRIPTION OF THE PREFERRED EMBODIMENT

Figure 1:
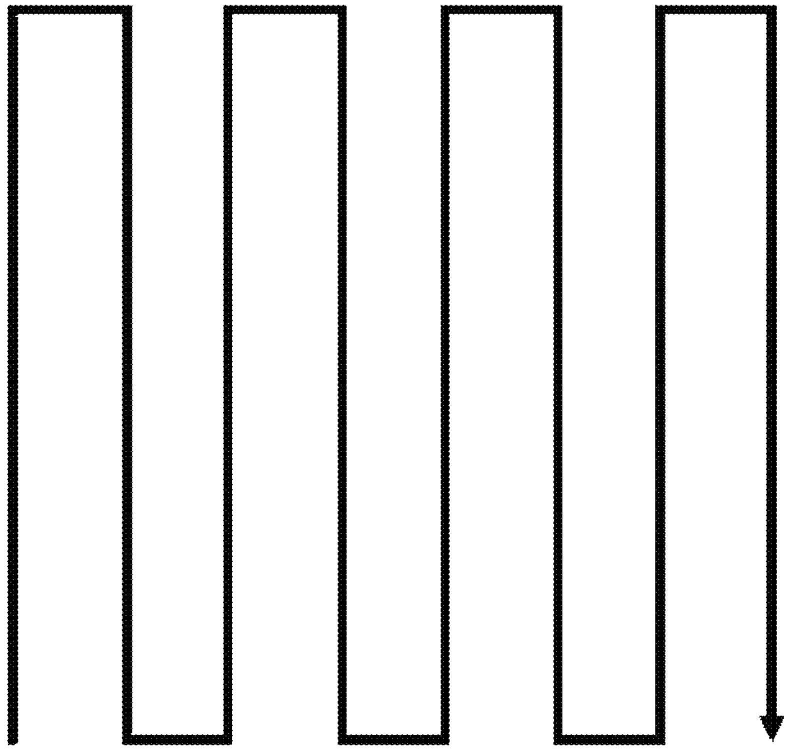
FIG. 1 shows a path in which a nozzle of a bio-ink discharge device is moved according to an embodiment of the present invention.

Hereinafter, the present invention will be described in detail.

The present invention provides a method for aligning and culturing cells in three dimensions.

The method for aligning and culturing cells in three dimensions includes mixing cells with a hydrogel to prepare a bio-ink, outputting the bio-ink while moving a nozzle of a discharge device to form an output product having a pattern having at least parallel portions, curing the output product, and culturing the cured product.

First, a bio-ink is prepared.

The bio-ink collectively refers to a material which may be applied to a bio-printing technique to produce a necessary structure, and includes a bio-derived material and a material for providing a biological environment in which the bio-derived material may perform a target function. In the present invention, the bio-ink may be prepared by mixing cells with a hydrogel, and if necessary, may additionally include other additives, such as a cell culture medium or a bioactive substance.

The cells may be cells to be neatly aligned and cultured in a certain direction, and may be cells to be differentiated, cells being differentiated, or cells already differentiated. Particularly, the cells may be cells constituting a textured tissue, for example, muscle cells, such as myoblasts or myotubes in particular, but are not limited thereto.

The hydrogel is a gel using an aqueous liquid containing water as a dispersion medium, and at this time, a dispersoid may be a hydrophilic polymer. The hydrophilic polymer may be cross-linked by a covalent or non-covalent bond to form a three-dimensional network structure, and due to excellent absorbency unique to the hydrophilic polymer, the hydrophilic polymer may absorb water in an aqueous environment and swell without being dissolved by the cross-linked structure. The hydrogel as described above is then cured later to serve as a support for maintaining a state in which the cells are aligned, and may be derived from nature, such as microorganisms, animals, plants, etc., or artificially synthesized. For example, the hydrogel may be obtained by dispersing one dispersoid or a mixture of two or more dispersoids, such as gelatin, gellan gum, collagen, agar, alginic acid, hyaluronic acid, carrageenan, gum arabic, gum ghatti, pullulan gum, mannan gum, locust bean gum, and xanthan gum, in a dispersion medium containing water. The hydrogel may have a concentration of 0.1 wt % to 15 wt %, for example, 0.5 wt % to 13 wt %, 1.0 wt % to 11 wt %, 3.0 wt % to 10 wt %, 4.0 wt % to 9.0 wt %, or 5.0 wt % to 8.0 wt %.

In addition, the cells may be mixed in a ratio of $1\times10^4$ cells to $1\times10^{12}$ cells, for example, $1\times10^5$ cells to $1\times10^{11}$ cells, $1\times10^6$ cells to $1\times10^{10}$ cells, or $1\times10^7$ cells to $1\times10^9$ cells per 1 mL of the hydrogel, and may be mixed with a hydrogel pre-heated to a temperature of 30° C. to 40° C., for example, 35° C. to 38° C.

In addition, the bio-ink prepared as described above is bioprinted to form an output product.

The bioprinting refers to forming a three-dimensional deposit through an automated or computer-assisted means provided with a bio-ink discharge device, such as a bio-printer, and for example, refers to forming a deposit having any suitable geometry, including circular, square, rectangular, triangular, polygonal, or irregular geometry by spraying a bio-ink from a bio-printer through a discharge device connected to a reservoir of the bio-ink. Particularly, forming a three-dimensional deposit with a bio-ink through the bio-printing as described above is called 3D-bioprinting. Therefore, the bioprinted output product may be a three-dimensional deposit, and in the output product having a three-dimensional structure as described above, the cells may also be disposed or arranged in three dimensions accordingly.

Figure 2:
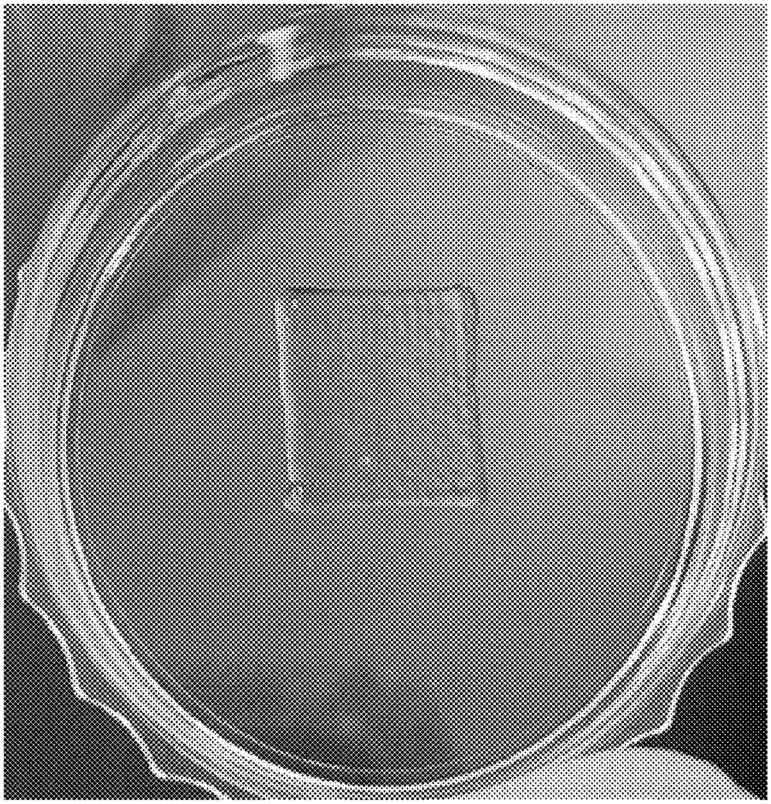
FIG. 2 is a photograph showing a cured product obtained by curing an output product formed by outputting a bio-ink while moving a nozzle of a bio-ink discharge device in the path as illustrated in FIG. 1 according to an embodiment of the present invention.

The bioprinting may be performed by outputting the bio-ink while moving a nozzle of the discharge device. Particularly, in the process of moving a nozzle of the discharge device, the bio-ink may be allowed to be continuously discharged, and the nozzle of the discharge device may move in a certain direction, particularly in one direction. Therefore, the output product formed by outputting the bio-ink while moving the nozzle of the discharge device may have a pattern having a shape in which at least portions of the pattern are parallel. In a specific embodiment of the present invention, the bio-ink was outputted while moving the nozzle of the discharge device in a path illustrated in FIG. 1, and as a result, an output product having a parallel pattern as illustrated in FIG. 2 was obtained.

In the bioprinting process as described above, the nozzle of the discharge device may be 20 gauge (G) to 30 gauge (G), for example, 21G to 29G, 22G to 28G, 23G to 27G, or 24G to 26G, and through a nozzle having the above-described size, the bio-ink may be discharged at a pressure of 30 kPa to 100 kPa, for example, 35 kPa to 90 kPa, 40 kPa to 80 kPa, 45 kPa to 75 kPa, 50 kPa to 70 kPa, or 55 kPa to 65 kPa to form an output product.

Next, the three-dimensional output product formed as described above may be cured.

The curing refers to a process in which a hydrogel in the output product is cross-linked by a covalent or non-covalent bond, and if necessary, according to the type of the hydrogel, a material which induces or promotes the cross-linking as described above may be used as a curing agent. The curing agent may be transglutaminase, genipin, glutaraldehyde, diisocyanates, carbodiimides, a calcium salt (e.g., calcium chloride), thrombin, or the like, and according to the type of the hydrogel, an appropriate curing agent may be selectively used. For example, when the hydrogel is gelatin, the curing agent may be transglutaminase, and when the hydrogel is alginic acid, the curing agent may be a calcium salt such as calcium chloride.

The curing may be performed by treating the output product with a solution containing the curing agent, and may be performed at an appropriate temperature (e.g., 30° C. to 40° C., particularly at a temperature of 35° C. to 38° C.) for a sufficient time (e.g., 5 minutes to 60 minutes, 10 minutes to 50 minutes, 20 minutes to 40 minutes, particularly 25 minutes to 35 minutes).

Through the curing process as described above, a hydrogel in an output product is cross-linked to form a three-dimensional network structure, and cells may be stably disposed using the three-dimensional network structure as a support, and the cells may be fixed in a three-dimensionally aligned state according to a pattern which is formed in the output product and which has a shape in which at least portions of the pattern are parallel.

The cured product which has been cured as described above may be cultured.

The curing is a process of proliferating cells included in the cured product, and through the curing, the size and number of the cells included in the cured product are increased. The culturing may be performed using a medium appropriate for culturing according to the type of the cells, and the appropriate culture medium according to the type of the cells may be appropriately selected and used by a person skilled in the art. Meanwhile, when the cells are fully differentiated cells such as myotubes, it is possible to align and culture the cells by the culturing process as described above.

Meanwhile, when the cells are cells to be differentiated or being differentiated, the cells may further undergo a process of additionally differentiating a culture which has been cultured as described above. When the cells are cells to be differentiated or being differentiated but simply cultured, only the size and number of the cells may have been increased while still being in a state to be differentiated or a state of being differentiated, so that cells in the culture may be fully differentiated through the differentiation process as described above. For example, when the cells are myoblasts, the cells may be differentiated into myotubes through the process as described above. The differentiating as described above may be performed by further culturing the culture using a differentiation induction medium, and the differentiation induction medium may also be appropriately selected and used by a person skilled in the art according to the type of the cells.

When the cells are finally cultured or further differentiated through the method for aligning and culturing cells of the present invention as described above, cells with increased size and number are arranged at a high density in the cured product along a three-dimensional structure of the hydrogel, so that the texture of a tissue formed by the cells may be simulated in some cases. For example, when myotubes are cultured according to the present invention, or myoblasts are cultured according to the present invention and then further differentiated, muscle cells are disposed at a high density in the cured product according to a pattern having a shape in which at least portions of the pattern are parallel, so that a unique texture of a muscle tissue may be reproduced.

Hereinafter, the present invention will be described in detail with reference to Examples.

However, the following Examples are merely illustrative of the present invention, and the present invention is not limited by the following Examples.

Example 1

Forming Output Product in which Cells are Three-Dimensionally Aligned 1 ml of Dulbecco's phosphate-buffered saline (DPBS) containing 0.67% of gellan gum and 6.00% of gelatin was pre-heated at 37° C., and then pellets of $1\times10^8$ cells of C2Cl2 cells, which are myoblasts of a mouse, were added thereto and suspended to produce a bio-ink. The above-produced bio-ink was mounted on an output barrel of a 3D bioprinter, and the bio-ink was outputted at a pressure of 60 kPa while moving a 25-gauge (G) nozzle in the path as illustrated in FIG. 1 to form an output product having a pattern as shown in FIG. 1 on a culture dish, and then, the output product was treated with DPBS containing 5% of transglutaminase and reacted at 37° C. for 30 minutes. As a result, as illustrated in FIG. 2, a cured product with a thickness of 0.25 to 0.5 mm in which a pattern having the same shape as the path of FIG. 1 was formed was obtained.

Figure 3:
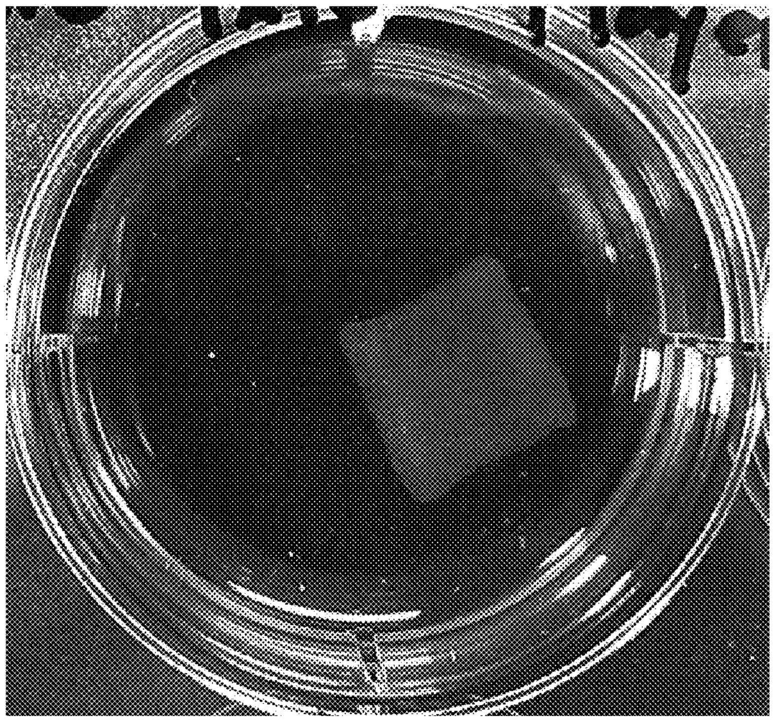
FIG. 3 is a photograph of a process of culturing and additionally differentiating a cured product obtained by curing an output product according to an embodiment of the present invention.

Then, the cured product in a gel state was removed from the bottom of the culture dish and then placed into a low attachment plate, and using Dulbecco's modified eagle medium (DMEM) containing 10% of fetal bovine serum (FBS) and 1% of antibiotic antimycotic solution, floating culture was performed in three dimensions as illustrated in FIG. 3 under the conditions of 37° C. and 5 days while supplying 5% of C02. Next, replacement was made with a differentiation induction medium of DMEM containing 2% of horse serum (HS) and 1% of antibiotic antimycotic solution, and culturing was performed again for 8 days in the same manner.

Example 2

Identifying Alignment State of Cells

The culture which was differentiated in Example 1 was washed 3 times with phosphate buffer saline (PBS), treated with 4% of paraformaldehyde solution, and fixed at 37° C. for 15 minutes, and then washed again 3 times with PBS. Then, the culture was treated with PBS containing 0.5% of Triton X-100, reacted at room temperature for 15 minutes, washed 3 times with PBS, treated with PBS containing 2% of bovine serum albumin (BSA), and then reacted at room temperature for an hour. Then, an MyHC antibody (primary) was treated by being mixed with PBS containing 0.1% of BSA at a ratio of 1:400, reacted at 4° C. overnight, and then washed 3 times with PBS, and then a secondary antibody and DAPI were treated by being mixed in a PBS solution containing 0.1% of BSA at a ratio of 1:200, and then reacted at room temperature for 2 hours. Next, treating with PBS containing 0.1% of Tween 20 and reacting for 5 minutes was repeated 3 times, and the culture was observed with a fluorescence microscope.

Figure 4:
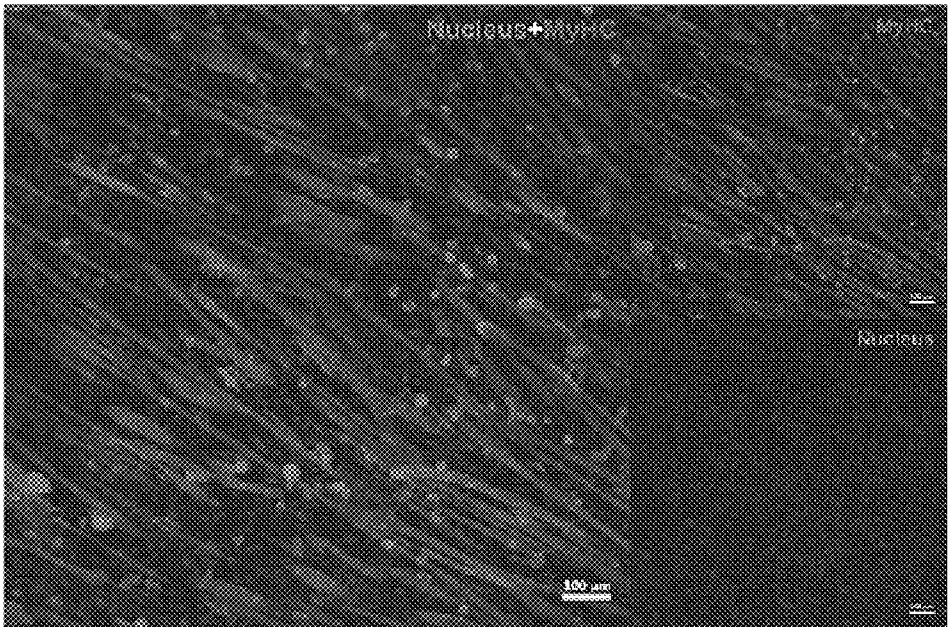
FIG. 4 is a photograph showing the result of immunostaining a differentiated culture to identify the alignment state of cells in the culture.

As a result, as illustrated in FIG. 4, it was confirmed that myotubes differentiated from myoblasts were cultured in a neatly aligned state according to the path of FIG. 1.

In the above, preferred embodiments of the present invention have been exemplarily described, but the scope of the present invention is not limited to the specific embodiments as described above, and may be appropriately changed within the scope as set forth in the claims by those skilled in the art.

The invention claimed is:

1. A method for aligning and culturing cells in three dimensions, the method comprising:
- mixing cells with a hydrogel comprising unmodified gelatin as a dispersoid to prepare a bio-ink;
- outputting the bio-ink while moving a nozzle of a discharge device to form an output product having a pattern having at least parallel portions on a culture dish;
- curing the output product by treating the output product with a solution containing transglutaminase or glutaraldehyde to make the unmodified gelatin crosslinked after the output product is formed; and
- removing the cured product from the culture dish and floating culturing the cured product in a liquid culture medium.

2. The method of claim 1, wherein the cells are either myoblasts or muscle cells.

3. The method of claim 1, wherein the hydrogel is pre-heated to a temperature of 30 to 40° C.

4. The method of claim 1, wherein the hydrogel further comprises gellan gum as a dispersoid.

5. The method of claim 1, wherein the bio-ink is outputted at a pressure of 30 kPa to 100 kPa from a nozzle of 20 gauge (G) to 30 gauge (G).

6. The method of claim 1, further comprising floating culturing the previously floating-cultured, cured product in a differentiation induction medium.

7. The method of claim 1, wherein the curing the output product is performed at a temperature of 30° C. to 40° C. for 5 minutes to 60 minutes.

8. The method of claim 1, wherein the floating culturing the cured product comprises placing the cured product into a low attachment plate.

9. The method of claim 6, wherein the cells are myoblasts, and the myoblasts are differentiated into myotubes by the floating culturing in the differentiation induction medium.

* * * * *